United States Patent [19]
McLean et al.

[11] Patent Number: 5,623,052
[45] Date of Patent: Apr. 22, 1997

[54] SYNTHETIC PEPTIDE LUNG SURFACTANTS HAVING COVALENTLY BONDED ANTIOXIDANTS

[75] Inventors: Larry R. McLean, Wyoming; J. Vincent Edwards, Cincinnati, both of Ohio

[73] Assignee: Merrell Pharmaceuticals Inc., Cincinnati, Ohio

[21] Appl. No.: 502,722

[22] Filed: Jul. 14, 1995

Related U.S. Application Data

[63] Continuation of Ser. No. 77,802, Jun. 21, 1993, abandoned, which is a continuation-in-part of Ser. No. 923,092, Jul. 31, 1992, abandoned.

[51] Int. Cl.$^6$ ............................. A61K 38/00; C07K 5/00; C07K 7/00
[52] U.S. Cl. ............................................. 530/330; 530/331
[58] Field of Search ................................ 530/330, 331, 530/402; 514/17, 18

[56] References Cited

U.S. PATENT DOCUMENTS 4,861,756  8/1989  Jackson .

FOREIGN PATENT DOCUMENTS

| | | |
|---|---|---|
| 0348967 | 6/1989 | European Pat. Off. . |
| 0512899 | 4/1992 | European Pat. Off. . |
| 0529568 | 8/1992 | European Pat. Off. . |
| 9308824 | 5/1993 | WIPO . |

OTHER PUBLICATIONS

McLean, et al., Biochimica et Biophysica Acta 1167:289–95 (1993).
McLean, et al., Am. Rev. Respir Dis vol. 147:4622–465 (1993).
McLean, et al., Biochimica et Biophysica Acta 1166:31–38 (1993).
McLean, et al., Biochemistry vol. 30(1):31–37 (1991).
McLean et al., *J of Pharm & Exp Therap.*, vol. 266, No. 2, pp. 551–556, 1993.
McLean et al., *Am. Phys. Society*, pp. L292–L300 (1992).
Travis, Am. Rev. Respir. Dis. 135:773–774 (1987).
Heffner, et al., Am. Rev. Respir. Dis 140:531–554 (1989).
Cochrane, et al., Science, ol. 254:566–568 (1991).
Waring, et al., Peptide Research 2(5):308–323 (1989).
McLean, et al., The Journal of Pharmacology and Experimental Therapeutics, vol. 266, No. 2, pp. 551–556 (1993) "Role of the Hydrophobic Face of Amphiphathic Alpha–Helical Peptides in Synthetic Pulmonary Surfactants".

*Primary Examiner*—Avis M. Davenport
*Attorney, Agent, or Firm*—Kenneth J. Collier

[57] ABSTRACT

Synthetic pulmonary surfactants having antioxidant properties consisting of a complex of a polypeptide of 3–4 amino acid residues, with an antioxidant moiety, and a lipid consisting of one or more of the lipids associated with natural pulmonary surfactant were prepared. These surfactants are useful in the treatment of respiratory distress syndrome.

11 Claims, 1 Drawing Sheet succinyl-Leu-Leu-Glu-Lys-Leu-Leu-Glu-Trp-Leu-Lys-NH$_2$

HBB-Aoc-Glu-Trp-Ala-Lys-NH$_2$

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note=
            " Xaa=N-alpha-[N-(8-hydroxy-di-t-butyl-benzoyl)-am
            ino octanoic]-glutamic acid (HBB-Aoc-Glu)"

( i x ) FEATURE:
        ( A ) NAME/KEY: Modified-site
        ( B ) LOCATION: 3
        ( D ) OTHER INFORMATION: /note="Xaa=2-amino-isobutyric acid
        ( A i b )"

( i x ) FEATURE:
        ( A ) NAME/KEY: Modified-site
        ( B ) LOCATION: 4
        ( D ) OTHER INFORMATION: /note="Xaa=lysin-1-amide"

( x i ) SEQUENCE DESCRIPTION: SEQ ID NO:1:

Xaa  Trp  Xaa  Xaa
    1

( 2 ) INFORMATION FOR SEQ ID NO:2:

( i ) SEQUENCE CHARACTERISTICS:
        ( A ) LENGTH: 4 amino acids (B) TYPE: amino acid
(D) TOPOLOGY: linear (ii) MOLECULE TYPE: peptide (ix) FEATURE:
 (A) NAME/KEY: Modified-site
 (B) LOCATION: 1
 (D) OTHER INFORMATION: /note=
  "Xaa=N-alpha-[N-(8-hydroxy-di-t-butyl-benzoyl)-am
  ino octanoic]-glutamic acid (HBB-Aoc-Glu)"

(ix) FEATURE:
 (A) NAME/KEY: Modified-site
 (B) LOCATION: 4
 (D) OTHER INFORMATION: /note="Xaa=lysin-1-amide"

(xi) SEQUENCE DESCRIPTION: SEQ ID NO:2:

Xaa  Trp  Glu  Xaa
1

(2) INFORMATION FOR SEQ ID NO:3:

(i) SEQUENCE CHARACTERISTICS:
  (A) LENGTH: 5 amino acids
  (B) TYPE: amino acid
  (D) TOPOLOGY: linear (ii) MOLECULE TYPE: peptide (ix) FEATURE:
  (A) NAME/KEY: Modified-site
  (B) LOCATION: 1
  (D) OTHER INFORMATION: /note=
   "Xaa=N-alpha-[N-(6-hydroxy-2,5,7,8-tetramethyl-ch
   roman-2- carboxylic acid)-amino octanoic]"

(ix) FEATURE:
  (A) NAME/KEY: Modified-site
  (B) LOCATION: 1
  (D) OTHER INFORMATION: /note="(cont'd) -glutamic acid
  (Trl-Aoc-Glu)"

(ix) FEATURE:
  (A) NAME/KEY: Modified-site
  (B) LOCATION: 4
  (D) OTHER INFORMATION: /note="Xaa=2-amino-isobutyric acid
  (Aib)"

(ix) FEATURE:
  (A) NAME/KEY: Modified-site
  (B) LOCATION: 5
  (D) OTHER INFORMATION: /note="Xaa=lysin-1-amide"

(xi) SEQUENCE DESCRIPTION: SEQ ID NO:3:

Xaa  Glu  Trp  Xaa  Xaa
1         5

(2) INFORMATION FOR SEQ ID NO:4:

(i) SEQUENCE CHARACTERISTICS:
  (A) LENGTH: 4 amino acids
  (B) TYPE: amino acid
  (D) TOPOLOGY: linear (ii) MOLECULE TYPE: peptide (ix) FEATURE:
  (A) NAME/KEY: Modified-site
  (B) LOCATION: 1
  (D) OTHER INFORMATION: /note=
   "Xaa=N-alpha-[N-(8-hydroxy-di-t-butyl-benzoyl)-gl
   utamic acid (HBB-G..."

(ix) FEATURE:
  (A) NAME/KEY: Modified-site (B) LOCATION: 3
(D) OTHER INFORMATION: /note="Xaa=2-amino-isobutyric acid (Aib)"

(ix) FEATURE:
(A) NAME/KEY: Modified-site
(B) LOCATION: 4
(D) OTHER INFORMATION: /note="Xaa=lysin-1-amide"

(xi) SEQUENCE DESCRIPTION: SEQ ID NO:4:

Xaa Trp Xaa Xaa
1

(2) INFORMATION FOR SEQ ID NO:5:

(i) SEQUENCE CHARACTERISTICS:
(A) LENGTH: 4 amino acids
(B) TYPE: amino acid
(D) TOPOLOGY: linear (ii) MOLECULE TYPE: peptide (ix) FEATURE:
(A) NAME/KEY: Modified-site
(B) LOCATION: 1
(D) OTHER INFORMATION: /note=
" Xaa=N-alpha-[N-(8-hydroxy-di-t-butyl-benzoyl)-am
ino octanoic]-glutamic acid (HBB-Aoc-Glu)"

(ix) FEATURE:
(A) NAME/KEY: Modified-site
(B) LOCATION: 4
(D) OTHER INFORMATION: /note="Xaa=lysin-1-amide"

(xi) SEQUENCE DESCRIPTION: SEQ ID NO:5:

Xaa Trp Ala Xaa
1

SYNTHETIC PEPTIDE LUNG SURFACTANTS HAVING COVALENTLY BONDED ANTIOXIDANTS

CROSS-REFERENCE TO RELATED APPLICATION

This is a continuation, of application Ser. No. 08/077,802, filed Jun. 21, 1993 now abandoned, which is a continuation-in-part of application Ser. No. 07/923,092, filed Jul. 31, 1992, now abandoned,, which is herein incorporated by reference.

FIELD OF THE INVENTION

This invention relates to the synthesis of a series of 3 to 4 amino acid polypeptides having antioxidants covalently linked to the peptide either directly or through a linker region. These modified peptides are useful as synthetic lung surfactants having useful antioxidants structurally as part of the peptide. Also described are the preparation of mixtures of these polypeptides with lipids, the method for production of same, and pharmaceutical compositions which are effective in the treatment of mammalian respiratory distress syndromes.

BACKGROUND OF THE INVENTION

The lungs exist in a delicate balance between toxic oxidants and the protective activities of antioxidant defense systems. An imbalance in this system, either through an increase in oxidants or a dysfunction of the protective antioxidant defense systems, can lead to pathophysiological events in the lung causing pulmonary dysfunction. One type of pulmonary dysfunction in which an increase in oxidants can contribute is respiratory distress syndrome (RDS).

Infantile respiratory distress syndrome is a leading cause of death in the first 28 days of life. Infantile RDS strikes 1 in 100 babies worldwide and about 10 percent die. The syndrome rarely occurs in term infants but is generally associated with immaturity and low-birth weight (under 2 kg). Adult RDS shows similar clinical characteristics and pathophysiology to the infantile disease and is generally managed in an intensive care facility. The adult disease has diverse etiologies, many resulting from lung insults, such as diffuse infections, aspiration of the gastric contents, inhalation of irritants and toxins, and pulmonary edema arising from such sources as narcotic overdose.

RDS is correlated with an absence or dysfunction of the lung surfactant which coats the alveoli of the lungs where gas exchange occurs, and has been associated with oxygen centered free radicals in the lung or lung cavity known as oxidants, such as superoxide radicals, hydroxyl radicals, hydrogen peroxide which can generate hydroxyl radicals, and lipid peroxides, which have been implicated in cellular injury (Heffner, et al., *Am. Rev. Respir. Dis.* 104: 531–554 1989); (Halliwell, *FASEB J.* 1: 358–364 1987).

Synthetic lung surfactant of larger polypeptides having antioxidant moieties, have been described in U.S. patent application Ser. No. 07/789,918 filed filed Nov. 4, 1991 which is herein incorporated by reference. However, the present invention provides an effective synthetic lung surfactant having antioxidant properties to shortened peptides of 3–4 amino acids having the ability to inhibit oxidation of susceptible compounds into oxidants. The shortened lung surfactants provide a more efficient and more cost effective means of producing therapeutics. The present novelty of the invention resides in the ability to effectively reduce the peptide to 3–4 amino acids with the retention of surfactant properties and effectively deliver the peptide attached to a covalently bonded antioxidant.

Some synthetic lung surfactant preparations have added therapeutic agents such as Vitamin E to surfactant preparations as a separate component (U.S. Pat. No. 4,765,987; PCT Publication No. WO 90/11768; PCT publication no. WO 90/07469). However, in the present invention the antioxidants are not a separate component but are actually incorporated into a polypeptide. An advantage of incorporating the antioxidant into the polypeptide is that instead of having a three component mixture (lipid, polypeptide and antioxidant), a two component mixture is available. This can be a significant advantage in testing for efficacy for a marketable pharmaceutical where a variety of dosages and formulations must be tested for each component. Additionally, a two component formulation is easier to manufacture.

The polypeptides of the present invention may be used singly in mixtures with lipid or in combination in mixtures of lipid wherein the polypeptide comprises a minor component of the surfactant mixture. The composition of the present invention may be prepared in high purity and in a standardized fashion as it is a defined mixture of synthetic components. Also, the components are not derived from animal sources which minimizes the risk of contamination by viruses and bacteria.

A helical wheel representation of an amphipathic α-helical ten-residue peptide (for description of the amphipathic α-helical peptide see McLean, L. R. et al. *Biochem.*, 1991, 30, 31) is used to develop a model for three and four residue peptides. When looking down the barrel of the α-helix, the side chains of the residues indicate a hydrophobic face and a hydrophilic face on the helix. A four residue peptide represents a single turn of this α-helix with the required hydrophobic and hydrophilic face present. A three residue peptide represents a constricted turn of the α-helix with the hydrophobic and hydrophilic face still present.

SUMMARY OF THE INVENTION

The present invention comprises synthetic lung surfactants consisting of a complex of a polypeptide and lipids wherein the polypeptide has the following formula 1:

$$X-A_1-A_2-A_3-A_4-Y \qquad 1$$

or an optically active isomer or pharmaceutically acceptable salt thereof; wherein $A_1$ is a bond or negatively charged amino acid selected from Glu or Asp;

$A_2$ is a hydrophobic amino acid selected from Trp, Tyr, Phe, His, Val, Leu, or Ile;

$A_3$ is Aib, Glu, Gln, Leu, Ala, Orn or a bond; and $A_4$ is a positive charged amino acid selected from Lys, Arg, or His;

X is of formula Da or Db:

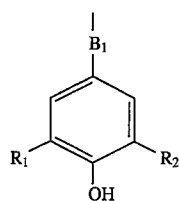
Da or

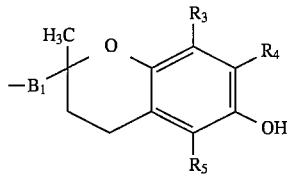

wherein, $B_1$ is B, —C(O)—, —B—C(O)—, —C(O)—NH—B—C(O)—; and B is a bond, $C_{1-16}$ alkylene, or $C_{2-16}$ alkenylene; and wherein each $R_1$, $R_2$, $R_3$, $R_4$, $R_5$, $R_6$ and $R_7$ is independently a $C_{1-6}$ alkyl;

Y is a carboxyl substituent of $A_4$ selected from hydroxy, amino, alkylamino, and alkoxy groups; and wherein, when $A_3$ is a bond, $A_1$ and $A_2$ may be interchanged.

In addition the present invention comprises synthetic lung surfactants consisting of a complex of a polypeptide and lipids wherein the polypeptide has the following formula 2:

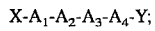

or an optically active isomer or pharmaceutically acceptable salt thereof; wherein $A_1$ is a bond or Glu;

$A_2$ is Trp or Glu;

$A_3$ is Aib, Glu, Gln, Leu, Ala or Orn; and $A_4$ is Lys;

X is of formula Da or Db:

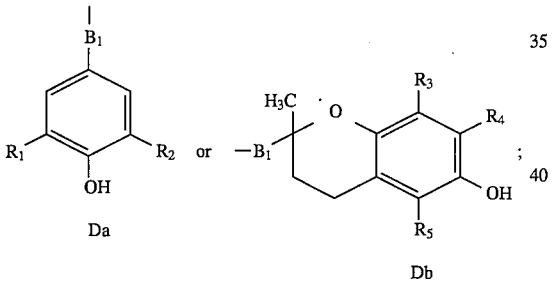

wherein $B_1$ is B, —C(O)—, —B—C(O)—, —C(O)—NH—B—C(O)—; and B is a bond, $C_{1-16}$ alkylene, or $C_{2-16}$ alkenylene; and wherein each $R_1$, $R_2$, $R_3$, $R_4$, $R_5$, $R_6$ and $R_7$ is independently a $C_{1-6}$ alkyl; and Y is a carboxyl substituent of $A_4$ selected from hydroxy, amino, alkylamino, and alkoxy groups.

Further the peptides of this invention may be associated with a lipid, comprised of one or more of the type associated with natural pulmonary surfactant.

These polypeptide-lipid complexes and their pharmaceutical compositions are useful in treating mammalian respiratory distress syndrome.

BRIEF DESCRIPTION OF TABLES

Figure 1:
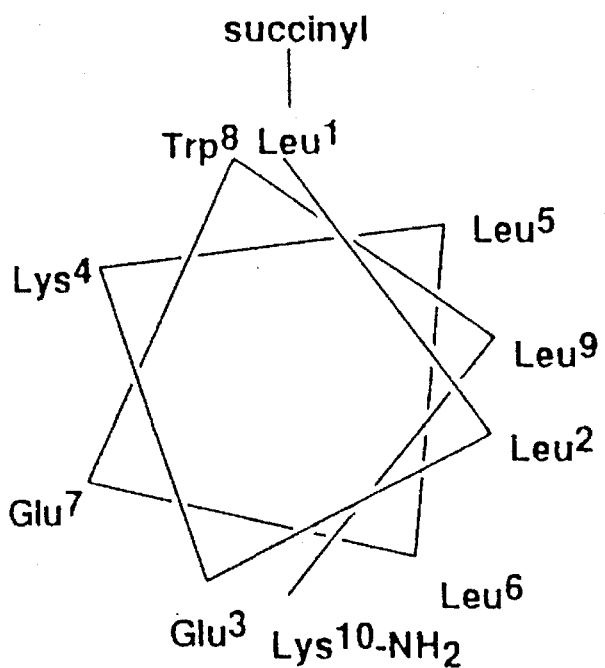
FIG. 1 is a helical wheel representation of a ten-residue peptide surfactant used to develop a model for short peptides. The view is down the barrel of the helix and the side chains of the residues are indicated in their positions relative to the axis of the helix. The hydrophobic face includes the residues to the right in the drawing which are $Trp^8$, $Leu^1$, $Leu^5$, $Leu^9$, $Leu^2$ and $Leu^6$. The hydrophilic face includes the charged residues $Lys^4$, $Glu^7$, $Glu^3$ and $Lys^{10}$.
Figure 2:
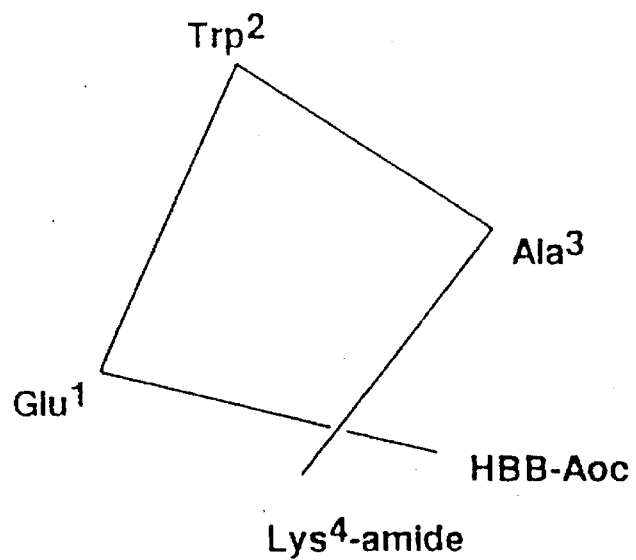
FIG. 2 is an example of a tetrapeptide antioxidant designed on the basis of a single turn of the helical wheel projection of the ten-residue peptide shown in FIG. 1. The hydrophobic face of the FIG. 1 peptide has been replaced by $Trp^2$, $Ala^3$, HBB-Aoc which present a sufficient hydrophobic face to anchor the peptide to the lipid. The hydrophilic charged face has been replaced by $Glu^1$ and $Lys^4$.

Table I shows the results from amino acid analysis of the synthesized peptides.

Table II shows the results of pressure-volume experiments showing the effectiveness of compounds in the adult rat lung model.

DETAILED DESCRIPTION OF THE INVENTION

The following common abbreviations of the naturally occurring amino acids are used throughout this specification:

Ala or A—alanine
Val or V—valine
Leu or L—leucine
Ile or I—isoleucine
Phe or F—phenylalanine
Trp or W—tryptophan
Met or M—methionine
Ser or S—serine
Tyr or Y—tyrosine
Asp or D—aspartic acid
Glu or E—glutamic acid
Gln or Q—glutamine
Thr or T—threonine
Gly or G—glycine
Lys or K—lysine
Arg or R—arginine
Asn or N—asparagine
Nle—norleucine
Orn—ornithine
hArg—homoarginine
Nva—norvaline
Aib—amino-isobutyric acid The natural amino acids, with the exception of glycine, contain a chiral carbon atom. Unless otherwise specifically indicated, the optically active amino acids, referred to herein, are of the L-configuration. Once the antioxidant moiety of the present invention is added to the peptide, stereoisomers can be formed. The present invention comprises mixtures of such stereoisomers as well as the isolated stereoisomer. As is customary, the structure of peptides written out herein is such that the amino terminal end is on the left side of the chain and the carboxy terminal end is on the right side of the chain.

When two amino acids combine to form a peptide though a typical amide bond, a molecule of water is released, and what remains of each amino acid is called a "residue". The amide linkage can also occur when X is linked to a subsequent amino acid or to an amide bond isoster. A residue is therefore an amino acid that lacks a hydrogen atom of the terminal amino group, and lacks the hydroxyl group of the terminal carboxyl group. Using accepted terminology, a dash (–) in front of (indicating loss of a water) a three letter code for an amino acid or amino acid derivative indicates the amine bond of a residue.

"Alkyl" as used herein means a straight or branched chain hydrocarbon radical such as methyl, ethyl, propyl, butyl, isopropyl, tert-butyl, sec-butyl, isopentyl, 1-methylbutyl and so on, depending upon the number of carbon atoms specified. "Acyl" as used herein means a radical formed from an organic acid by removal of a hydroxyl group; the general formula is RCO— where R may be aliphatic, alicyclic, aromatic hydrocarbon or hydrogen (formyl group). The R group may be substituted. An example of an acyl group is succinyl.

As used herein the term "hydrophobic amino acid" means a nonpolar residue with an aliphatic hydrocarbon side chain such as Val, Leu or Ile; or a nonpolar residue with an aromatic group such as Phe, Tyr, Trp or His.

As used herein the term "negatively charged amino acid" means a polar residue with an acidic hydrophilic side chain such as Glu or Asp.

As used herein the term "positive charged amino acid" means a polar residue with a basic hydrophilic side chain such as Lys, Arg or His.

Peptides, where X has not been functionally modified by the designated antioxidant, can be synthesized by any suitable method such as solid phase sequential procedure, described hereafter. Preferred Markush groups are where, $R_1$, $R_2$, $R_6$ and $R_7$ are each tert-butyl, and each of $R_3$, $R_4$ and $R_5$ are methyl. Da is preferable to Db, and B is preferably —C(O)—NH—B—C(O)—, wherein B is a $C_8$ alkane;

X is referred to herein as "antioxidant moiety" because it is believed that X is that portion which confers antioxidant properties on the polypeptide. However, it is to be understood that X may have linkers to the polypeptide so that when antioxidant moieties attached to the polypeptide are described, it also includes the appropriate linkers, e.g., B, —C(O)—, B—C(O)—, C(O)—NH—B—C(O)—, etc.

There are many ways to form X. For example, amino acid derivatives can be acylated by an acylating agent formed from antioxidant compounds. To be an acylating agent, the antioxidant compounds can, for example, form a symmetrical anhydride or an active ester, e.g., N-hydroxybenzotriazole ester (HOBt ester). The acylating agent is then exposed to the unprotected functional nucleophile for the reaction to take place. This is preferably performed in solid phase peptide synthesis while the amino acid to receive the antioxidant moiety is part of the peptide attached to the resin.

Individual amino acids can also be modified prior to incorporation into the peptide by, for example, esterification, reductive alkylation, etc. Other modifications of amino acids and amino acid derivatives containing functional groups are well known in the art.

Preferred examples of antioxidant compounds found to be useful in reacting with amino acids or amino acid derivatives in the present invention are as follows:
1) HBB=3,5-di-t-butyl-4-hydroxybenzoic acid
2) HBP=3-(3',5'-di-tert-butyl-4-hydroxyphenyl)propionic acid
3) HBC=3,5-di-tert-butyl-4-hydroxycinnamic acid
4) HBA=2-(3',5'-di-t-butyl-4-hydroxyphenyl) acetic acid
5) di-HBA=2,2-di-(3',5'-di-t-butyl-4-hydroxyphenyl)acetic acid
6) Trl=6-hydroxy-2,5,7,8-tetramethylchroman-2-carboxylic acid—also known as Trolox Preferably HBB, HBP, HBC, HBA, di-HBA, and Trl are used when the functional group is either an alcohol group or an amino group. Within the group of linked surfactants a preferred grouping can be selected to form a more preferred grouping, such as, HBB and Trl.

The foregoing antioxidant compounds are commercially available or the synthesis known in the art, e.g., 3,5-di-t-butyl-4-hydroxyphenylacetic acid is described in Izv. Akad. Nauk SSSR, Ser. Khim., 358 1965 and 3,5-di-t-butyl-4-hydroxy-benzaldehyde is described in J. Org. Chem., 22, 1333 1957. Generally, any antioxidant compound may be used in the present invention which (1) can be attached to the polypeptide of the present invention, (2) exhibits antioxidant activity while attached to the polypeptide, and (3) permits the polypeptide to perform as described herein.

Trl-Glu—means a molecule having a peptide bond formed between trolox and a glutamyl residue; wherein the trolox is attached to the α-amino group of a Glutamic acid residue as shown below:

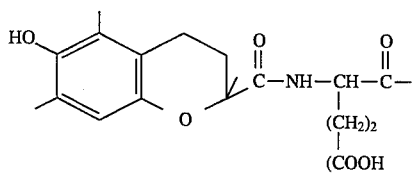

As shown by the Trl-Glu example, the antioxidant moiety, in this case where X=Db and B=a bond, together with a carbonyl group (C(O)—) can be attached to the α-amino terminus of polypeptide to form Db—C(O)—$A_1$-$A_2$-$A_3$-$A_4$-Y.

The polypeptides of this invention can be prepared by a variety of procedures readily known to those skilled in the art such as solution phase chemistry. A preferred method is the solid phase sequential procedure which can use automated methods such as the ABI peptide synthesizer. In solid phase sequential procedure, the following steps occur: (1) a first amino acid, having a protected α-amino group, is bound to a resin support; (2) the carboxylic group of a second amino acid, having a protected α-amino group, is activated; (3) the first amino acid is deprotected with a reagent which permits the first amino acid to remain attached to the resin; and (4) coupling occurs between the α-amino group of the first amino acid and the activated carboxylic group of the second amino acid. These steps are repeated with new amino acid residues which permits the formation of the peptide. When the desired length of peptide has been formed, the peptide may be modified with an appropriately coupled antioxidant moiety prior to being cleaved from the resin, deprotected and isolated. Alternatively the protected peptide may be selectively removed from the resin, and the antioxidant moiety is coupled to the peptide prior to removal of protecting groups and isolation.

The resin support employed can be any suitable resin conventionally employed in the art for the solid phase preparation of polypeptides such as a polystyrene which has been cross-linked with from 0.5 to about 3 percent divinyl benzene, which has been either chloromethylated or hydroxymethylated to provide sites for ester formation with the initially introduced α-amino protected amino acid. Other suitable resin supports are pMHBA (Peptide International, Louisville, Ky.), RINK (Calbiochem, LaJolla, Calif.) and Sasrin (Biochem, Philadelphia, Pa.). The Sasrin resin requires a special ABI cycle for loading the first amino acid which is described in the ABI peptide synthesizer user's manual. The first amino acid, having a protected α-amino group, is attached to the resin as described in the Applied Biosystems Model 430A Peptide Synthesizer User's Manual, incorporated in its entirety herein.

Preferred methods of activating each added amino acid to the bound peptide chain include formation of a symmetrical anhydride or active ester of the each added α-amino, which has been appropriately protected. For example, an α-amino protected amino acid can be reacted with dicyclohexylcarbodiimide (DCC) in the presence of dichloromethane (DCM) to form the symmetrical anhydride. Alternatively, a HOBt active ester can be formed by dissolving Boc-amino acid (tert-butyloxycarbonyl-amino acid) and HOBt in DCC and chilling, adding additional DCC and warming the solution to room temperature. This solution is then added to the amino acid bound resin. This method of activation to form acylating agents may also be used for the antioxidant compounds.

If there are other functional groups present besides the α-amino group, those groups will generally have to be protected. Generally, the α-amino group and each of the side chain functional groups can be protected by different protecting groups so that one protecting group can be removed without removing the other protecting groups.

Among the classes of α-amino protecting groups contemplated for use with the present invention are (1) acyl type protecting groups such as: formyl, trifluoroacetyl, phthalyl, toluenesulfonyl (tosyl), benzenesulfonyl, nitrophenylsulfenyl, tritylsulfenyl, o-nitrophenoxyacetyl and γ-chlorobutyryl; (2) aromatic urethan type protecting groups such as benzyloxycarbonyl and substituted benzyloxycarbonyl such as p-chlorobenzyloxycarbonyl, p-nitrobenzyloxycarbonyl, p-bromobenzyloxycarbonyl, p-methoxybenzyloxycarbonyl, 1-(p-biphenyl)-1-methylethoxycarbonyl, α,α-dimethyl-3,5-dimethoxybenzyloxycarbonyl and benzylhydryloxycarbonyl; (3) aliphatic urethan protecting groups such as tert-butyloxycarbonyl (Boc), diisopropylmethoxycarbonyl, isopropyloxycarbonyl, ethoxycarbonyl and allyloxycarbonyl; (4) cycloalkyl urethan type protecting groups such as cyclopentyloxycarbonyl or 9-fluorenylmethoxycarbonyl (Fmoc); (6) alkyl type protecting groups such as triphenylmethyl (trityl) and benzyl; (7) trialkylsilane groups such as trimethylsilane.

The selection of the α-amino protecting group, however, will depend upon the resin used, the target site functional group, the other functional groups present in the polypeptide and whether the amino acid derivative X can withstand cleavage from the resin with the cleavage reagent. For example, to prepare HBB-Aoc-Glu-Trp-Aib-Lys-NH$_2$, (SEQ ID NO: 1), a pMBHA resin is used, which produces a C terminal amino group, and the peptide is constructed using standard t-Boc chemistry on an ABI430A peptide synthesizer. The HBB moiety can be introduced as an HOBT active ester in order to attach HBB at the target site N-α-amino group of Glutamic acid. Anhydrous hydrofluoric acid (HF) can be used to simultaneously cleave the peptide from the resin and to remove the remaining protecting groups.

The selection of appropriate combination of protecting groups and reagents to selectively remove protecting groups is well known in the art. For example, see M. Bodanszky, PEPTIDE CHEMISTRY, A PRACTICAL TEXTBOOK, Springer-Verlag (1988); J. Stewart, et al., SOLID PHASE PEPTIDE SYNTHESIS, 2nd ed., Pierce Chemical Co. (1984).

Each protected amino acid or amino acid sequence is introduced into the solid phase reactor in about a four-fold excess and the coupling is carried out in the presence of a coupling agent such as in a medium of dimethylformamide: methylene chloride (1:1) or in dimethylformamide alone or methylene chloride alone. In cases where incomplete coupling occurs, the coupling procedure is repeated before removal of the α-amino protecting group, prior to the coupling of the next amino acid in the solid phase reactor. The success of the coupling reaction at each stage of the synthesis is monitored by the ninhydrin reaction as described by E. Kaiser, et al., *Analyt. Biochem.* 34, 595 (1970).

After the desired amino acid sequence has been obtained, the peptide is removed from the resin using any appropriate reagent which will not adversely effect the polypeptide. For example, anhydrous HF containing 5% anisole and 5% acetonitrile in 0.1% trifluoroacetic acid can be used to cleave the polypeptide from a pMBHA resin.

The polypeptides of Formula 1 can form pharmaceutically acceptable salts with any non-toxic, organic or inorganic acid. Illustrative inorganic acids which form suitable salts include hydrochloric, hydrobromic, sulphuric and phosphoric acid and acid metal salts such as sodium monohydrogen orthophosphate and potassium hydrogen sulfate. Illustrative organic acids which form suitable salts include the mono, di and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic and sulfonic acids such as methane sulfonic acid and 2-hydroxyethane sulfonic acid. Salts of the carboxy terminal amino acid moiety include the non-toxic carboxylic acid salts formed with any suitable inorganic or organic bases. Illustratively, these salts include those of alkali metals, as for example, sodium and potassium; alkaline earth metals, such as calcium and magnesium; light metals of Group IIIA including aluminum; and organic primary, secondary and tertiary amines, as for example, trialkylamines, including triethylamine, procaine, dibenzylamine, 1-ethenamine, N,N'-dibenzylethylenediamine, dihydroabietylamine, N-(lower)alkylpiperidine, and any other suitable amine.

The phospholipids of the protein-phospholipid complexes of this invention can be any phospholipid and this term as used herein includes the phosphoglycerides and the sphingolipids. Phosphoglycerides are those di-fatty acid esters of glycerol in which the remaining hydroxy group, a terminal hydroxy group, of the gylcerol moiety forms an ester with phosphoric acid. Commonly the phosphoric acid moiety of the phosphoglycerides forms a second ester with an alcohol such as ethanolamine, serine, choline, or glycerol. Sphingolipids are those mono-fatty acid esters of sphingosine or dihydrosphingosine in which the hydroxy group at the 1-position forms an ester with the choline ester of phosphoric acid. The preferred lipids of the protein-phospholipid complexes of this invention comprise dipalmitoylphosphatidylcholine (DPPC), phosphatidylcholine molecules containing acyl chains of other lengths and degrees of saturation (PC), cardiolipin (CL), phosphatidylglycerols (PG), phosphatidylserines (PS), fatty acids (FA), and triacylglycerols (TG). DPPC comprises the major component of the lung surfactant mixture while PC, CL, PG, PS, FA, and TG comprise minor components. Suitable fatty acids for use in the phospholipids of this invention are long chain carboxylic acids (generally having eight or more carbon atoms), typically unbranched. The fatty acids can be either saturated or unsaturated. Representative fatty acids are lauric, myristic, palmitic, and oleic acids.

Pharmaceutical preparations of the polypeptide or the protein-phospholipid complexes of this invention can be prepared as a dry mixture or in an aqueous suspension, in some instances containing small amounts of organic solvents, such as, for example, ethanol or trifluoroethanol, detergents, such as, for example, sodium dodecyl sulfate or sodium deoxycholate, salts, such as calcium chloride or sodium chloride, carbohydrates, such as glucose, dextrose or mannitol, and amino acids, such as glycine and alanine. Where the pharmaceutical composition is made into liquid form, stabilizers, preservatives, osmotic pressure regulators, buffering agents, and suspending agents of the liquid may be added. If desired, suitable germicides may also be added. The pH of the aqueous suspension may vary between 2 and 10 and may be adjusted with acids and bases, such as, for example, hydrochloric acid, sodium phosphate, or sodium hydroxide. The dry mixture may be reconstituted in an aqueous solution containing pharmaceutically acceptable salts, organic solvents, and detergents. The aqueous preparation may be dialyzed, filtered, or chromatographed to exchange the suspending medium with a pharmaceutically acceptable medium prior to use. The preparation may be administered as a dry powder, an aqueous suspension, or as an aerosol directly into the lungs of the distressed subject. The pharmaceutical composition of the present invention may be charged in hermetically sealed containers such as vials and ampules and be preserved sterilely. The composition may be stored in a vial or ampule separately from a vial or ampule containing the suspension buffer and the dry or hydrated composition may be mixed with the suspension buffer prior to use.

Lipid constitutes from 50 to 99.9% of the lung surfactant preparation. Suitable lipids include DPPC, PC, CL, PG, PS, FA, and TG. DPPC comprises the major lipid species and is present in concentrations of 60 to 100% of the total lipid weight. The remaining lipids are present in minor concentrations. PC, CL, PG and PS may comprise up to 30% of the lipids, and FA and TG may comprise up to 10% of the lipid weight. The fatty acyl chains of the minor lipid components may be saturated or unsaturated and of any chain length. Chain lengths of 12 to 16 carbon atoms and up to 2 unsaturated bonds are preferred. The preferred lipid composition is 85–100% DPPC plus 0–15% of PG. Most preferred is pure DPPC.

The lipid components of the synthetic lung surfactant are commonly found in mammalian lung surfactant and are available from common industrial sources in high purity. The polypeptide components are prepared by solid-phase peptide synthesis by methods familiar to those skilled in the art. Mixtures of the lipids of the invention with proteins isolated from mammalian lung lavage have been shown to be effective in treating neonatal RDS. However, mixtures of these lipids with synthetic peptides in lung surfactant preparations has only recently been reported (McLean, et al.).

Lipids are suspended as liposomes by methods familiar to those skilled in the art; i.e., wherein initially lipids are mixed in a volatile organic solvent or mixtures of solvents, such as mixtures of chloroform and methanol or trifluoroethanol. The organic solvent is removed by evaporation under nitrogen, argon, or under vacuum. An aqueous solution which may contain organic and inorganic acids, bases, and salts, and saccharides such as dextrose is added to the dry lipid mixture to attain a final concentration of 0.1 to 100 mg of DPPC per ml. In general, it is preferable, but not necessary to warm the mixture to 35°–50° C., mix vigorously, and incubate for up to 2 hours at 25°–50° C. Then, peptide or a mixture of peptides is added as a dry powder or suspended in an aqueous solution in some cases containing a suitable organic solvent, such as ethanol or trifluoroethanol, or a denaturing agent, such as guanidinium hydrochloride or urea, which improves the solubility of the peptide in the aqueous suspension. Association of peptide and lipid may be promoted at a particular pH, thus the pH of the aqueous solution may vary from 2 to 10. The preferred method for mixing peptide and lipid is to add dry peptide to lipid in water at 45°–50° C. and to mix by bath ultrasonication at 45°–50° C. for 30–90 minutes, then freeze-dry and store at −20° C.

Lipids can optionally be mixed with a suitable detergent such as octylglucoside or sodium deoxycholate at a weight ratio of from 1 to 20 parts of detergent per part of DPPC in water, an aqueous buffer, or saline solution at concentrations from 1 to 100 mg DPPC/ml. Then, peptide is added as a dry powder or suspended in an aqueous solution with or without an organic solvent, denaturing agent, or detergent. The mixture is then dialyzed, filtered, centrifuged or chromatographed to remove the detergent.

Preferably, lipids and peptides are mixed in a volatile organic solvent with or without a small amount of water. The volatile solvent is evaporated under a stream of nitrogen or argon, in a vacuum oven, or by rotary evaporation either before or after addition of an aqueous solvent.

The mixture of lipid and peptide prepared by one of the methods described above is incubated for up to 2 hours, preferably at 35°–50° C. with sonic irradiation. The mixture may then be dialyzed, filtered, or chromatographed to replace the aqueous medium with a pharmaceutically acceptable medium, although this is not necessary. In some cases, efficacy is improved by separating unreacted lipid or peptide from associated lipid and peptide by ultracentrifugation, filtration, or chromatography. The mixture may then be lyophilized or aerosolized.

When the polypeptide-phospholipid complexes of this invention are used in the treatment of neonatal respiratory distress syndrome, a physiological condition which results from the inability of the lungs of premature infants to produce pulmonary surfactant, the complexes act as an antioxidant and synthetic pulmonary surfactants and either replace the natural, missing surfactant or augment the lack of sufficient natural surfactant. Treatment is continued until the infant's lungs produce a sufficient amount of natural, pulmonary surfactant so as to render further treatment unnecessary.

The preparations are preferably those suitable for endotracheal administration, that is as a liquid suspension, a dry powder, or an aerosol. For a liquid suspension, the dry mixture or the mixture in aqueous suspension is mixed with suitable agents, such as water, saline solutions, dextrose, and glycerol to produce a pharmaceutically effective composition. Preferred liquid suspensions will contain 0.8 to 1.0 weight per cent of sodium chloride and will be 1–20 mM, preferably in calcium ion. The preparation is then filter sterilized. In general, the preparation comprises 1 to 100 mg of DPPC per ml and is administered at a dose of 0.2 to 5 ml/kg. To prepare a dry mixture, the aqueous suspension is lyophilized. The aerosol is prepared from a finely divided dry powder suspended in a propellant, such as lower alkanes and fluorinated alkanes, such as Freon. The aerosol is stored in a pressurized container.

For example, the surfactant (polypeptide of the present invention and lipid complex) is administered, as appropriate to the dosage form, by endotracheal tube, by aerosol administration, or by nebulization of the suspension or dry mixture into the inspired gas. The surfactant is administered in one or multiple doses of 10 to 200 mg/kg. The preferred method of administration is as a suspension of peptide and lipid in physiological saline solution at a concentration of 5–10 mg of surfactant per ml through an endotracheal tube, achieving a dose of 50–100 mg/kg.

The polypeptide of the present invention is administered to treat a subject. "Subject" means a mammal, for example, but not limited to, a human being.

The following examples show some methods of preparation for the polypeptide, polypeptide/lipid complex and starting materials of the present invention. The present invention is not limited to the following examples nor to these methods of preparation.

Abbreviations used in the examples not previously defined are as follows:

| TBDMS | Tetrabutyldimethylsilyl |
|---|---|
| SEt | Ethylthio |
| Suc | Succinyl |
| TFA | Trifluoroacetic acid |
| Bzl | Benzyl |
| Ot—Bu | t-butyl ether; | which accompany standard Boc chemistry and standard Fmoc chemistry: that chemistry used with the ABI peptide synthesizer respectively for the Boc cycles and the Fmoc cycles.

EXPERIMENTAL CHEMICAL PROCEDURES

Example 1

Peptide Synthesis and other Chemicals. Peptides were synthesized on a 0.5 mmol scale by solid-phase methods on an Applied Biosystems Inc. (Foster City, Calif.) Model 430-A peptide synthesizer. p-methylbenzoxyhydrylamine (pMBHA) resin was used to give C-terminal amides on cleavage. N$\alpha$-t-Boc (t-butyloxycarbonyl) amino acids with side chain protection Cys(ethylthio), Glu(benzyl) and Lys(2-chlorobenzyloxycarbonyl) from Peptides International were double-coupled via their preformed symmetrical anhydrides. The antioxidant group, was coupled by activating the acid of the antioxidant to form the symmetrical anhydride. Antioxidants, such as HBB (3,5, di-tert-butyl-4-hydroxy benzoic acid) were placed at the amino terminus of the peptide by preactivating the HBB acid to form the corresponding symmetrical anhydride. Generally the antioxidant was double or triple coupled to assure complete reaction. For example HBB required three couplings to achieve complete incorporation. Additional couplings were performed as determined based on ninhydrin tests. N$\alpha$-t-Boc groups were removed with 50% trifluoroacetic acid (TFA) in methylene chloride and neutralized with 10% diisopropylethylamine (DEA) in dimethyl formamide. The peptides were cleaved from the resin and deprotected in anhydrous HF containing 5% anisole and 5% dimethyl sulfide at −5° C. for 45 min. HF was removed in vacuo and the peptide extracted from the resin with 50% aqueous acetonitrile. The combined extracts were frozen and lyophilized and purified by reverse phase preparative HPLC on a Rainin Dynamax (21.4×250 mm) $C_{18}$ column at 40 mL/min with an acetonitrile gradient in 0.1% aqueous TFA (pH 2) monitored at 214 nm. The major peak was collected and lyophilized. The purity (>97%) and identity of the synthetic peptides were confirmed by a single peak in the analytical high performance liquid chromatogram (HPLC), capillary zone electrophoresis, fast-atom bombardment mass spectrometry (FAB-MS) on a VG Analytical ZAB2-SE which gave single molecular ions consistent with the correct sequences, and amino acid analyses which were within 10% of the predicted values for each residue. L-$\alpha$-dipalmitoylphosphatidylcholine (DPPC) (>99% pure) was from Avanti Polar Lipids (Birmingham, Ala.). Using these procedures the following peptides were synthesized; their analytical properties are found in Table 1.

1(A). Preparation of Polypeptide: HBB-Aoc-Glu-Trp-Aib-Lys-NH$_2$ (SEQ ID NO: 1) (HBB-Aoc=N$^\alpha$-hydroxy-di-t-butyl-benzoyl-aminoocatanoyl-)

Initially Aoc-Glu(OBzl)-Trp-Aib-Lys(N$^\epsilon$-2ClZ)-pMBHA was prepared by using a Lys(N$^\epsilon$-2ClZ)-pMBHA resin placed in ABI430A peptide synthesizer and synthesized using standard t-Boc chemistry. To synthesize peptide 1A, N$^\alpha$-hydroxy-di-t-butyl-benzoic acid (HBB) (501 mg), dimethylformamide (4 mL) and methylene chloride (4 mL) were combined and a dicyclohexylcarbodiimide solution (8 mL of a 0.5M solution in methylene chloride) was added and stirred for 5 minutes to give the symmetrical anhydride of HBB, which was then coupled to Aoc-Glu(OBzl)-Trp-Aib-Lys(N$^\epsilon$-2ClZ)-pMBHA in 10× excess per each of two couplings. The HBB-Aoc-Glu(OBzl)-Trp-Aib-Lys(N$^\epsilon$-2ClZ)-pMBHA protected peptide was cleaved from the resin and side chain protecting groups were removed by treating the HBB-peptide-resin in anhydrous HF containing 5% anisole and 5% dimethylsulfide at −5° C. for 1 hour. The peptide was then extracted from the resin with 50% acetonitrile in 0.1% trifluoroacetic acid, frozen and lypohilized. The peptide was then purified by reverse phase HPLC to give the title compound.

1(B). Preparation of DPPC Complex with Polypeptide Described in Example 1(A)

Peptide 1(A) is prepared as described above. DPPC (25 mg) in 1 ml of chloroform is dried under a stream of nitrogen and dried under vacuum to remove traces of organic solvent. To the dry lipid mixture is added 3 ml of water. The preparation is incubated for 1 hour at 45° C. Then, 0.5 mg of dry peptide 1(A) is added to the aqueous preparation. The preparation is sonicated in a bath ultrasonicator at 45° C. for 2 hours. The resulting lipid-peptide mixture is lyophilized and stored at 4° C. for up to one month. Prior to testing, 9 ml of 0.9% NaCl, 20 mM HEPES buffer, pH 7.40 is added. The preparation is incubated for 1 hour at 45° C. with periodic mixing.

Example 2

2(A). Preparation of Polypeptide: HBB-Aoc-Glu-Trp-Glu-Lys-NH$_2$ (SEQ ID NO: 2) (HBB-Aoc=N$^\alpha$-hydroxy-di-t-butyl-benzoyl-aminoocatanoyl-)

Aoc-Glu(OBzl)-Trp-Glu(OBzl)-Lys(N$^\epsilon$-2ClZ)-pMBHA was prepared by using a Lys(N$^\epsilon$-2ClZ)-pMBHA resin placed in ABI430A peptide synthesizer and synthesized using standard t-Boc chemistry. To synthesize peptide 2A, N$^\alpha$-hydroxy-di-t-butyl-benzoic acid (HBB) (501 mg), dimethylformamide (4 mL) and methylene chloride (4 mL) were combined and a dicyclohexylcarbodiimide solution (8 mL of a 0.5M solution in methylene chloride) was added and stirred for 5 minutes to give the symmetrical anhydride of HBB, which was then coupled to Aoc-Glu(OBzl)-Trp-Glu-(OBzl)-Lys(N$^\epsilon$-2ClZ)-PMBHA in 4× excess per each of two couplings. The HBB-Aoc-Glu(OBzl)-Trp-Glu(OBzl)-Lys(N$^\epsilon$-2ClZ)-pMBHA protected peptide was cleaved from the resin and side chain protecting groups were removed by treating the HBB-peptide-resin in anhydrous HF containing 5% anisole and 5% dimethylsulfide at −5° C. for 1 hour. The peptide was then extracted from the resin with 50% acetonitrile in 0.1% trifluoroacetic acid, frozen and lypohilized. The peptide was then purified by reverse phase HPLC to give the title compound.

2(B). Preparation of DPPC Complex with Polypeptide Described in Example 2(A)

Peptide 2(A) was mixed with DPPC essentially as described under Example 1.

Example 3

3(A). Preparation of Polypeptide: (Trl-Aoc-Glu-Trp-Aib-Lys-NH$_2$ (Trl-Aoc-=N$\alpha$-hydroxy-di-t-butyl-benzoyl-aminoocatanoyl) (SEQ ID NO: 3)

Aoc-Glu(OBzl)-Trp-Aib-Lys(N$^\epsilon$-2ClZ)-pMBHA was prepared by using a Lys(N$^\epsilon$-2ClZ)-pMBHA resin placed in ABI430A peptide synthesizer using standard t-Boc chemistry.

To synthesize peptide 3A, 6-hydroxy-2,5,7,8,-tetramethylchroman-2-carboxylic acid (Trolox) (501 mg), dimethylformamide (4 mL) and methylene chloride (2.5 mL) were combined and a dicyclohexylcarbodiimide solution (8 mL) of a 0.5M solution in methylene chloride) was added and stirred for 5 minutes to give the symmetrical anhydride which was then coupled to Aoc-Glu(OBzl)-Trp-Aib-Lys(N$^\epsilon$-2ClZ)-pMBHA in 10× excess per each of two couplings.

To cleave Trl-Aoc-Glu(OBzl)-Trp-Aib-Lys(N$^\epsilon$-2ClZ)-pMBHA from the resin and remove side chain protecting groups, the peptide was treated with anyhdrous HF, 5% anisole and 5% dimethylsulfide at −5° C. for 1 hour. The Trl-peptide was extracted from the resin with 50% acetonitrile in 0.1% trifluoroacetic acid, frozen and lypohilized. The Trl-peptide was purified by reverse phase HPLC to give the title compound.

3(B). Preparation of DPPC Complex with Polypeptide Described in Example 3(A)

Peptide 3(a) was prepared with DPPC essentially as described in Example 1b.

Example 4

4(A). Preparation of Polypeptide: HBB-Glu-Trp-Aib-Lys-NH$_2$ (SEQ ID NO: 4) (HBB=N$^\alpha$-hydroxy-di-t-butyl-benzoyl)

Peptide 4(A) is prepared in a manner essentially analogous to the preparation of peptide 1(A).

4(B). Preparation of DPPC Complex with Polypeptide Described in Example 4(A)

Peptide 4(A) is mixed with DPPC essentially as described under Example 1.

Example 5

5(A). Preparation of Polypeptide: HBB-Aoc-Glu-Trp-Ala-Lys-NH$_2$ (SEQ ID NO: 5) (HBB-Aoc=N$^\alpha$-hydroxy-di-t-butyl-benzoyl-aminoocatanoyl-)

Peptide 5(A) is prepared in a manner essentially analogous to the preparation of peptide 1(A).

5(B). Preparation of DPPC Complex with Polypeptide Described in Example 4(A)

Peptide 5(A) is mixed with DPPC essentially as described under Example 1.

TABLE 1

ANALYTICAL PROPERTIES OF PEPTIDES SYNTHESIZED
FABS-MASS SPECTROMETRY ANALYSIS OF PEPTIDES 1–7

| SEQ ID No: | PEPTIDE | FAB MS | AAA |
|---|---|---|---|
| 1 | HBB—Aoc—Glu—Trp—Aib—Lys—NH$_2$ | [M + H]$^+$ = 920.6 | @85% |
| 2 | HBB—Aoc—Glu—Trp—Glu—Lys—NH$_2$ | [M + H]$^+$ = 963.6 | @62% |
| 3 | Trl—Aoc—Glu—Trp—Aib—Lys—NH$_2$ | [M + H]$^+$ = 920.6 | @89% |
| 4 | HBB—Glu—Trp—Aib—Lys—NH$_2$ | [M + H]$^+$ = 778.97 | @78% |
| 5 | HBB—Aoc—Glu—Trp—Ala—Lys—NH$_2$ | [M + H]$^+$ = 904 | @76% |

PREPARATION OF ANTIOXIDANT MOIETIES

The following antioxidant starting materials may be used as described in the preceding examples.

Example 6

Preparation of Starting Material Antioxidant Compound: 3-t-Butyl-5-methyl-4-hydroxybenzoic acid Charge a reaction vessel with a suspension of sodium hydride (4.74 g, 0.198 mol) in anhydrous ethylene glycol dimethyl ether (150 mL). Add, by dropwise addition, a solution of 2-t-butyl-6-methylphenol (0.1 mol) in ethylene glycol dimethyl ether (150 mL). Warm to 50°–60° C. for 1.5 hours then introduce carbon dioxide through a gas-disparging tube below the surface of the reaction mixture for 20 hours. Cool to 5° C. and destroy the excess sodium hydride carefully with methyl alcohol (30 mL). After hydrogen evolution ceases, adjust the pH of the reaction mixture to 2 with 1N hydrochloric acid. Dilute with water (1.6 L) and collect the title compound by filtration.

Example 7

Preparation of Starting Material Antioxidant Compound: (6-Hydroxy-7-t-butyl-5-isopropyl-8-propyl-chroman-2-yl)acetic acid Mix magnesium turnings (45 mg, 1.85 mmol) and 1-chloro-2,2-dimethylpropane (74.6 mg, 0.7 mmol) in anhydrous ether (9 mL). Heat and stir vigorously, then add, by dropwise addition, 1,2-dibromoethane (156 mg, 0.839 mmol) in anhydrous ether (1.5 mL). Reflux for 12 hours, place under an argon atmosphere and cool to 0°–5° C. Add, by dropwise addition, a solution of isobutyryl chloride (0.533 mmol) in anhydrous diethyl ether (1.5 mL). Stir at 0°–5° C. for 1.5 hours, pour into a mixture of ice and concentrated hydrochloric acid (0.15 mL) and separate the organic phase. Wash with ethyl acetate, 5% aqueous sodium carbonate and brine. Dry ($MgSO_4$) and evaporate the solvent in vacuo to give 2,2-6-trimethyl-4-heptanone.

Dissolve vinylmagnesium chloride (0.7 mmol) in anhydrous diethyl ether (1 mL), place under an argon atmosphere and cool to 1°–5° C. Add, by dropwise addition, a solution of butyryl chloride (0.533 mmol) in anhydrous diethyl ether (1.5 mL). Stir at 0°–5° C. for 1.5 hours, pour into a mixture of ice and concentrated hydrochloric acid (0.15 mL) and separate the organic phase. Wash with water, 5% aqueous sodium carbonate and brine. Dry ($MgSO_4$) and evaporate the solvent in vacuo to give propyl vinyl ketone.

Dissolve 2,2-6-trimethyl-4-heptanone (0.4 mol) in methanol (10 mL) and add potassium tert-butoxide (12 g. 0.1 mol). Add, by dropwise addition, a solution of propyl vinyl ketone (0.2 mol) in methanol (10 mL). Stir for 10 minutes and portion between ethyl ether and brine. Separate the organic phase and wash with brine until neutral. Dry ($Na_2SO_4$) and evaporate the solvent in vacuo to give 2-propyl-3-t-butyl-5-isopropylbenzoquinone.

Dissolve 2-propyl-3-t-butyl-5-isopropylbenzoquinone (10 mmol), 1,1,3,3-tetramethyldisiloxane (1.79 mL, 10 mmol) and iodine (0.05 g) in methylene chloride (30 mL). Stir at reflux for 30 minutes and extract with 1N sodium hydroxide (30 mL). Acidify the aqueous phase with concentrated hydrochloric acid and extract into ethyl acetate (4×10 mL), dry ($Na_2SO_4$) and evaporate the solvent in vacuo to give 2-propyl-3-t-butyl-4-hydroxy-5-isopropylphenol.

Dissolve 2-propyl-3-t-butyl-4-hydroxy-5-isopropylphenol (2.0 mol) and trimethyl orthoformate (0.3 L) in methanol (1.2 L) under a nitrogen atmosphere and degas. Place under a nitrogen atmosphere and cool to 3° C. and add concentrated sulfuric acid (5 mL). Add, by dropwise addition, methyl vinyl ketone (340 mL, 4.0 mol) and stir without cooling for 44 hours. Pour into aqueous sodium hydrogen carbonate and extract into ethyl ether. Dry ($MgSO_4$) and evaporate the solvent in vacuo to give 2-methoxy-2-methyl-7-t-butyl-5-isopropyl-8-propyl-chroman-6-ol.

Dissolve 2-methoxy-2-methyl-7-t-butyl-5-isopropyl-8-propyl-chroman-6-ol (2 mol) in pyridine (600 mL) and add acetic anhydride (900 mL). Degas and stir under a nitrogen atmosphere for 18 hours. Pour into ice/water and stir for 3 hours. Extract into ethyl ether, dry ($MgSO_4$), evaporate the solvent in vacuo and purify by chromatography to give 2-methoxy-2-methyl-7-t-butyl-5-isopropyl-8-propyl-chroman-6-yl-acetate.

Dissolve 2-methoxy-2-methyl-7-t-butyl-5-isopropyl-8-propyl-chroman-6-yl-acetate (2 mol) in acetone (2.5 L) and add water (2 L) followed by concentrated hydrochloric acid (16.6 mL). Distill the solvent from the stirred mixture until the head temperature reaches 90° C. Cool the suspension, dilute with ethyl ether and wash with aqueous sodium hydrogen carbonate. Dry ($MgSO_4$), evaporate the solvent in vacuo and purify by chromatography to give 2-hydroxy-2-methyl-7-t-butyl-5-isopropyl-8-propyl-chroman-6-yl-acetate.

Suspend sodium hydride (47.2 g of 56% in mineral oil, 1.10 mol) in anhydrous tetrahydrofuran (1 L). Place under a nitrogen atmosphere and add, by dropwise addition, trimethyl phosphonoacetate (209.4 g, 1.15 mol). Stir the 25 minutes and add a solution of 2-hydroxy-2-methyl-7-t-butyl-5-isopropyl-8-propyl-chroman-6-yl-acetate (0.5 mol) in tetrahydrofuran (1 L). Stir at room temperature for 18 hour then heat at reflux for 4 hours. Cool, evaporate the solvent in vacuo and purify by chromatography to give the title compound.

BIOLOGICAL

Methods of testing the synthetic surfactant preparations for efficacy are well known in the art. For example, the synthetic surfactant preparations of the present invention can be tested in any appropriate manner such as in the adult rat lung model (Ikegami, et al., (1979) *Pediatr. Res.* 13, 777–780).

Pressure-volume characteristics of surfactant-depleted rat lungs are similar to those of lungs of infants with hyaline membrane disease and restoration of the pressure-volume relationship of the lung to normal is related to the amount of surfactant instilled in a dose dependent manner. (Bermel, M. S., et al., Lavaged excised rat lungs as a model of surfactant deficiency, *Lung* 162: 99–113 (1984)).

Example 8

Isolated Rat Lavaged Lung Model

The experimental procedures for animal preparation, pressure-volume curve registration and lung lavage are adapted from those described by Ikegami et al., *Pediatr. Res.* 11: 178–182 (1977) and *Pediatr. Res.* 13: 777–780 (1979, and Bermel et al, *Lung* 162: 99–113 (1984). Male Sprague Dawley rats (200–250 g) are anesthetized with sodium pentobarbital and exsanguinated. The trachea is cannulated and the thoracic organs are removed en bloc. After removal of the adventitious tissue, the trachea and lungs (~2 g) are suspended in saline (0.9%), placed in a vacuum chamber, and degassed according to the procedure of Stengel et al. the degassed lungs are suspended in saline in a 37° C., jacketed reservoir and the tracheal cannula is connected both to a water manometer and a glass syringe by a T-tube. The glass syringe is placed in an infusion/withdrawal pump. Lungs are rapidly inflated with air to 30 cm $H_2O$ pressure at the rate of 10 ml/min to minimize air trapping, and are maintained at this pressure for 10 min by intermittently adding air to the lungs. The total volume of air infused is recorded as the total lung capacity (TLC) which is generally 14–15 ml. The lungs are then deflated at a rate of 2.5 ml/min until zero pressure is attained. During deflation, pressure is read from the water manometer at 1 cm intervals and recorded. These data are used to construct a pressure-volume (P-V) or quasi-static compliance curve after correction for the P-V curve of the apparatus. After degassing and equilibration, the lungs are rendered surfactant-deficient by repeated lavage with 5 ml/g lavage buffer (0.9% NaCl, 10 mM HEPES, pH 7.4). The procedures of degassing, equilibrating, and lavaging are repeated (15–20 times) until the pressure-volume curve had become distinctly sigmoidal in shape and the volume of air remaining in the lungs at 5 cm $H_2O$ pressure is less than or equal to 3 ml. At this point, the lungs are considered surfactant-deficient. For testing, 2 ml of 0.9% NaCl, 10 mM HEPES buffer, pH 7.4, are added to the dry lung surfactants (25 mg of phospholipid; 100–125 mg/kg) and the mixture is vortexed, flushed with nitrogen and incubated for 1 h at 45° C. The mixture is then vortexed again, degassed if foamy, and 2 ml of the test mixture are introduced into and withdrawn from the lungs four times by syringe. When the test mixture is reintroduced to the lungs for the fifth time, it is allowed to remain in the lungs. This procedure is adopted to encourage even distribution of the material throughout the lung. The lungs are degassed, allowed to equilibrate at 37° C. for 5 min, and a P-V measurement is performed. Lungs are studied while supported in saline at 37° C. as opposed to ambient temperature since the physical characteristics of the surfactants may be dependent upon temperature. Canine lung surfactant is administered in a similar manner except that the surfactant is heated for only 5 min. Data are presented in terms of the % TLC. The deflation limbs of the pressure-volume (P-V) curves in adult rat lungs are analyzed by calculating the total lung capacities (% TLC) at 5 and 10 cm $H_2O$ pressure ($PC_5$ and $PC_{10}$). Comparisons are based on per cent restoration=$(PC_{5(sufficient)}-PC_{5(test)})\times 100/(PC_{5(sufficient)}-PC_{5(deficient)})$ and made by one-way analysis of variance using the general linear models procedure with specific contrasts of the means (SAS Institute Inc., Cary, N.C.). Lavage and treatment with test mixtures did not produce a change in the absolute TLC of greater than 6%.

RESULTS

The preparations administered to the rat had a translucent appearance. The deflation limb of the pressure-volume (P-V) curve in adult rat lungs was analyzed by calculation of the per cent of total lung capacity (TLC) at 5 cm $H_2O$ pressure ($PC_5$) and the TLC at 10 cm $H_2O$ ($PC_{10}$). The restoration based upon the $PC_5$ values was used to compare the test mixtures. DPPC alone had no significant effect on the pressure-volume (P-V) curves of the lavaged lung. Activities of peptide-DPPC mixtures are indicated in Table 2.

TABLE 2

Efficacy of Synthetic Surfactants in The Adult Rat Lavaged Lung Model

| Mixture | n | $PC_5$ (% TLC) | $PC_{10}$ (% TLC) | RESTORATION % |
|---|---|---|---|---|
| sufficient | 50 | 68 ± 1 | 87 ± 1 | 100 |
| deficient | 50 | 17 ± 1 | 45 ± 1 | 0 |
| DPPC | 4 | 13 ± 1 | 31 ± 2 | −11 ± 8 |
| SEQ ID No: 1<br>HBB—Aoc—Glu—Trp—Aib—Lys—$NH_2$ + DPPC | 2 | 48 ± 5 | 73 ± 3 | 65 ± 5 |
| SEQ ID No: 2<br>HBB—Aoc—Glu—Trp—Glu—Lys—$NH_2$ + DPPC | 3 | 52 ± 2 | 75 ± 2 | 83 ± 5 |
| SEQ ID No: 3<br>Trl—Aoc—Glu—Trp—Aib—Lys—$NH_2$ + DPPC | 2 | 33 ± 2 | 59 ± 2 | 43 ± 6 |
| SEQ ID No: 5<br>HBB—Aoc—Glu—Trp—Ala—Lys—$NH_2$ + DPPC | 3 | 55 ± 4 | 77 ± 2 | 81 ± 7 |

What is claimed is:
1. A polypeptide of formula:

$$X-A_1-A_2-A_3-A_4-Y$$

or an optically active isomer or pharmaceutically acceptable salt thereof; wherein $A_1$ is a bond or Glu;
$A_2$ is Trp;
$A_3$ is Aib, Glu, or Ala; and
$A_4$ is Lys;
X is of formula Da or Db:

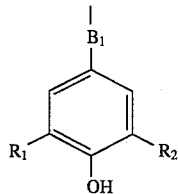

Da or

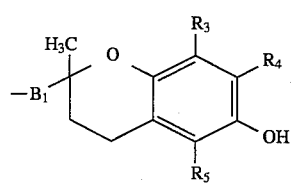

Db wherein $B_1$ is B, —C(O)—, —B—C(O)—, —C(O)—NH—B—C(O)—; and B is a bond, $C_{1-16}$ alkylene, or $C_{2-16}$ alkenylene; and wherein each $R_1$, $R_2$, $R_3$, $R_4$, $R_5$, $R_6$ and $R_7$ is independently a $C_{1-6}$ alkyl; and Y is a carboxyl substituent of $A_4$ selected from hydroxy, amino, alkylamino, and alkoxy groups.

2. A polypeptide as in claim 1, in which $A_3$ is a Aib.
3. A polypeptide as in claim 1, in which $A_3$ is a Ala.
4. A polypeptide as in claim 1, wherein Y is an amino.
5. A polypeptide as in claim 1, in which X is Da.
6. A polypeptide as in claim 1, in which each of $R_1$ and $R_2$ is tert-butyl.
7. A polypeptide as in claim 1, which is HBB-Aoc-Glu-Trp-Aib-Lys-NH$_2$. (SEQ ID NO: 1).
8. A polypeptide as in claim 1, which is HBB-Aoc-Glu-Trp-Glu-Lys-NH$_2$. (SEQ ID NO: 2).
9. A polypeptide as in claim 1, which is Trl-Aoc-Glu-Trp-Aib-Lys-NH$_2$. (SEQ ID NO: 3).
10. A polypeptide as in claim 1, which is HBB-Glu-Trp-Aib-Lys-NH$_2$. (SEQ ID NO: 4).
11. A polypeptide as in claim 1, which is HBB-Aoc-Glu-Trp-Ala-Lys-NH$_2$. (SEQ ID NO: 5).

* * * * *